United States Patent
Lane

(10) Patent No.: US 9,366,654 B2
(45) Date of Patent: Jun. 14, 2016

(54) METHOD OF MEASURING A CRYSTALLOGRAPHIC ORIENTATION OF AN OBJECT

(71) Applicant: ROLLS-ROYCE PLC, London (GB)

(72) Inventor: Christopher John Leslie Lane, Bristol (GB)

(73) Assignee: ROLLS-ROYCE plc, London (GB)

( * ) Notice: Subject to any disclaimer, the term of this patent is extended or adjusted under 35 U.S.C. 154(b) by 317 days.

(21) Appl. No.: 13/917,055

(22) Filed: Jun. 13, 2013

(65) Prior Publication Data

US 2014/0000369 A1      Jan. 2, 2014

(30) Foreign Application Priority Data

Jun. 27, 2012   (GB) .................................. 1211373.4

(51) Int. Cl.
G01H 5/00 (2006.01)
G01N 29/04 (2006.01)
G01N 29/07 (2006.01)

(52) U.S. Cl.
CPC .............. *G01N 29/041* (2013.01); *G01N 29/07* (2013.01); *G01N 2291/0289* (2013.01); *G01N 2291/0423* (2013.01); *G01N 2291/106* (2013.01)

(58) Field of Classification Search
CPC ............................ G01N 29/024; G01N 29/07
USPC ..................... 73/597, 598, 634, 641
See application file for complete search history.

(56) References Cited

U.S. PATENT DOCUMENTS

| 4,106,327 A | 8/1978 | Adler et al. |
| 5,467,655 A * | 11/1995 | Hyoguchi ................ B06B 1/04 73/579 |
| 5,955,671 A | 9/1999 | Gilmore et al. |
| 6,105,431 A * | 8/2000 | Duffill ................... G01N 29/11 73/596 |

FOREIGN PATENT DOCUMENTS

EP    1 850 126 A1    10/2007

OTHER PUBLICATIONS

Search Report issued in British Application No. 1211373.4 dated Sep. 27, 2012.

* cited by examiner

*Primary Examiner* — Hezron E Williams
*Assistant Examiner* — Tarun Sinha
(74) *Attorney, Agent, or Firm* — Oliff PLC

(57) ABSTRACT

A method of measuring a crystallographic orientation of an object using an ultrasonic transducer and a detector array including a plurality of ultrasonic detectors includes: determining a minimum distance between the transducer and the detector of the detector array closest to the transducer; placing the transducer and the detector array in contact with a surface of the object such that the transducer and the detector of the detector array closest to the transducer are separated by at least the minimum distance; using the transducer to generate an ultrasonic surface wave pulse in the surface of the object, the ultrasonic surface wave pulse having a pulse duration and including a longitudinal surface wave and a Rayleigh wave; and measuring a time of flight of a surface wave generated by the transducer between the transducer and each detector of the array to determine the crystallographic orientation of the object.

11 Claims, 4 Drawing Sheets

Fig.1a
Fig.1b
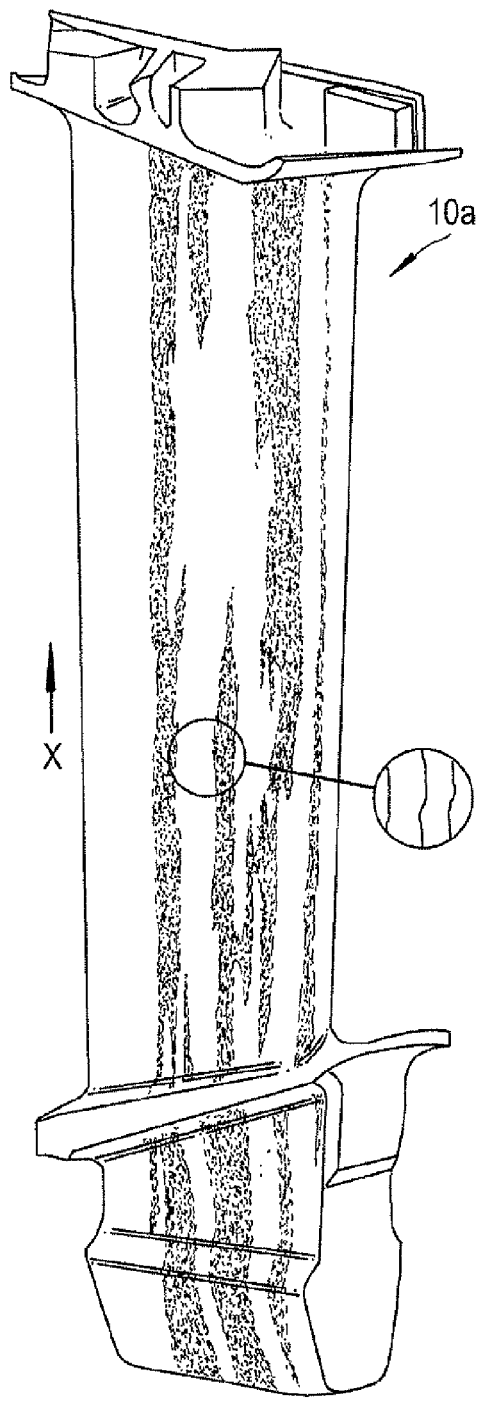
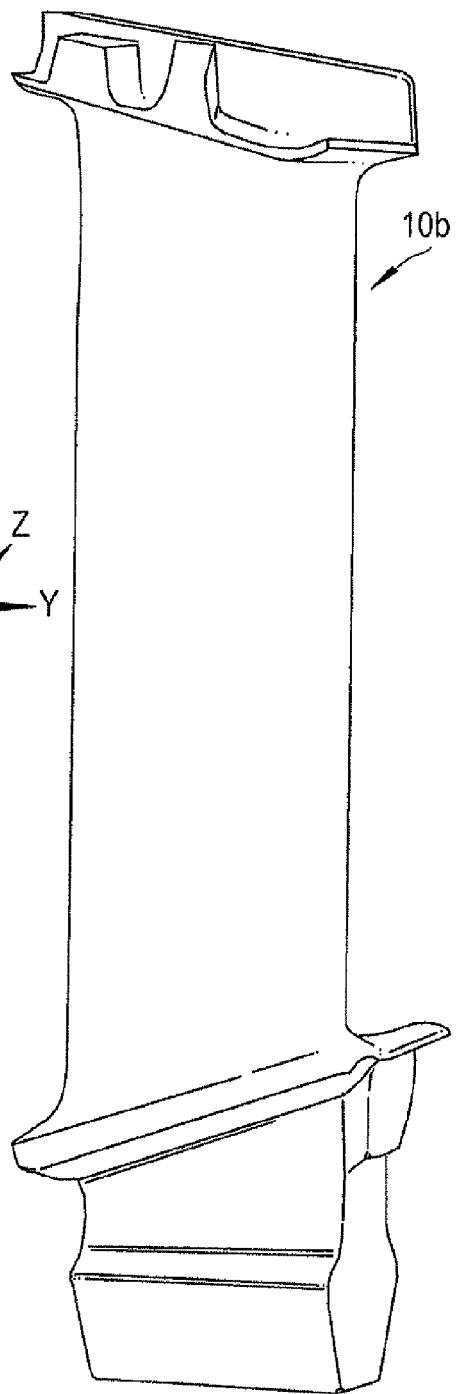

METHOD OF MEASURING A CRYSTALLOGRAPHIC ORIENTATION OF AN OBJECT

FIELD OF THE INVENTION

The present invention relates to a method of measuring a crystallographic orientation of an object, and an assembly for measuring a crystallographic orientation of an object.

BACKGROUND TO THE INVENTION

Ultrasonic defect inspection assemblies and methods are known for inspecting objects such as gas turbine engine components and the like for defects such as cracks, inclusions and porosity.

Prior ultrasonic inspection methods comprise using an ultrasonic wave generator (transducer) and one or more ultrasonic wave detectors separated by a known difference to measure the time-of-flight of propagating ultrasonic waves along known ray-paths to determine the velocity of the ultrasonic waves and therefore the local density and other properties of the material. In some materials, known as "isotropic" materials, the wave velocity is substantially constant in all directions. However, some materials, such as single crystal or directionally solidified metals or alloys, exhibit anisotropic properties due for example to the orientation of the crystal, such that the wave velocity varies according to direction of wave propagation. In order to reliably inspect objects comprising anisotropic materials, the orientation of the crystal must therefore be determined prior to defect inspection.

Ultrasonic inspection methods can be used to determine crystal orientation and therefore wave propagation velocity anisotropy by propagating ultrasonic waves along known ray paths in a number of directions. From these velocity measurements, a prediction of the crystallographic orientation can be made. A number of different ultrasonic methods have been devised. A first method, as described for example in U.S. Pat. No. 4,106,327, uses a transducer located on one surface of the object and a detector located on an opposite surface to measure the velocity of bulk ultrasonic waves through the object. However, the method described in U.S. Pat. No. 4,106,327 requires access to both sides of the object. A second method, such as that described in U.S. Pat. No. 5,955,671 utilizes reflectors in the object having known locations and reflective properties to reflect the wave generated by the transducer back to a detector located on the same face as the transducer (known as "pulse-echo" or "pitch-catch"). This is not always possible, since such known reflectors may not be present, which is the case for in situ inspections of gas turbine engine components for example.

A third orientation method has been suggested which comprises using ultrasonic surface-waves. Such a method would have the advantage of only requiring access to a single face of the material to perform the measurement without requiring the presence of a known reflector within the object. However, such methods have not previously been successful using conventional detector arrays, since the signals received by the detectors have been found to have a low signal to noise ratio. As such, the wave velocity of the surface-waves can often not be measured, and hence the orientation cannot be predicted accurately.

The present invention provides an ultrasonic inspection assembly which seeks to overcome these disadvantages.

SUMMARY OF THE INVENTION

According to a first aspect of the present invention there is provided a method of measuring a crystallographic orientation of an object using an ultrasonic transducer and a detector array comprising a plurality of ultrasonic detectors, the method comprising:

determining a minimum distance ($d_{min}$) between the transducer and a detector of the detector array closest to the transducer;

placing the transducer and the detector array in contact with a surface of the object such that the transducer and the detector of the detector array closest to the transducer are separated by at least the minimum distance ($d_{min}$);

using the transducer to generate an ultrasonic surface wave pulse in the surface of the object, the ultrasonic surface wave pulse having a pulse duration ($t_w$) and comprising a longitudinal surface wave and a Rayleigh wave; and measuring a time of flight of a surface wave generated by the transducer between the transducer and each detector of the array to determine the crystallographic orientation of the object;

wherein the minimum distance ($d_{min}$) is the distance at which the minimum time of flight of the Rayleigh wave ($t_R$) is at least the sum of the maximum time of flight of the longitudinal surface wave ($t_L$) and the maximum pulse duration ($t_w$).

The invention is enabled by the realization that the signal to noise ratio can be increased by specifying a minimum distance (dmin) between the transducer and the closest of the detectors in the detector array. The minimum distance has been found to comprise the distance at which the minimum time of flight of the Rayleigh wave (tR) is at least the sum of the maximum time of flight of the longitudinal surface wave (tL) and the maximum pulse duration (tw). By determining the minimum separation distance in this manner, the separation distance between the detectors can be chosen on the basis of a required resolution, while minimizing signal noise.

The ultrasonic surface wave pulse may have a centre frequency ($f_c$) and a pulse length (n) cycles, the longitudinal surface wave may have a minimum velocity in the object ($c_L$), and the Rayleigh wave may have a maximum velocity in the object ($c_R$). The minimum distance ($d_{min}$) may be determined by the formula:

$$d_{(min)} = \frac{n}{f_c}\left(\frac{c_L c_R}{c_L - c_R}\right)$$

The detector array may have a ring down time ($t_{rd}$). The distance ($d_{min}$) may be determined by the greater value of $d_{min}$ determined by the formulas:

$$d_{(min)} = \frac{n}{f_c}\left(\frac{c_L c_R}{c_L - c_R}\right)$$

and;

$$d_{(min)} = c_L\left(t_{rd} + \frac{n}{2f_c}\right)$$

The ultrasonic surface wave pulse may have a frequency in range 1 MHz to 15 MHz, and may have a frequency of approximately 5 MHz.

The object may comprise a nickel based alloy, and may comprise CMSX-4 alloy. The object may comprise a component of a gas turbine engine such as a turbine blade.

The detector array may comprise a 1-d array in which the detectors are arrayed in a row. Alternatively, the detector array may comprise a 2-d array in which the detectors are arrayed in at least two rows.

According to a second aspect of the invention there is provided crystallographic orientation measurement assembly, the assembly comprising:

an object having a crystallographic orientation;
an ultrasonic transducer configured to generate an ultrasonic surface wave pulse having a pulse duration ($t_w$), the ultrasonic surface wave pulse comprising a longitudinal surface wave and a Rayleigh wave; and
a detector array comprising a plurality of ultrasonic detectors; wherein the transducer and the detector of the detector array closest to the transducer are separated by at least a minimum distance ($d_{min}$), wherein the minimum distance ($d_{min}$) is the distance at which the minimum time of flight of the Rayleigh wave ($t_R$) is at least the sum of the maximum time of flight of the longitudinal surface wave (4) and the maximum pulse duration ($t_w$).

BRIEF DESCRIPTION OF THE DRAWINGS

Embodiments of the invention will now be described by way of example with reference to the accompanying drawings in which:

FIG. 1a shows a perspective view of a directionally solidified turbine blade;

FIG. 1b shows a perspective view of a single crystal turbine blade;

DETAILED DESCRIPTION

FIGS. 1a and b show turbine blades 10a and 10b made of a metallic alloy such as nickel super alloy. The turbine blades 10a, 10b are formed such that the alloy comprises directionally solidified crystals, or a single crystal respectively. In each case, the turbine blade 10a, 10b has a crystallographic orientation. Directionally solidified crystal materials are transversely isotropic, i.e. in the plane normal to a nominal X direction, the material is approximately isotropic. Therefore, the orientation can be represented by a single direction, represented in FIG. 1a by the arrow X, as shown in detail in the enlarged view of FIG. 1a. However, single crystal alloy blades, such as that shown in FIG. 1b have a cubic anisotropy, i.e. the crystal orientation has to be computed around the X, Y and Z axes.

Figure 2:
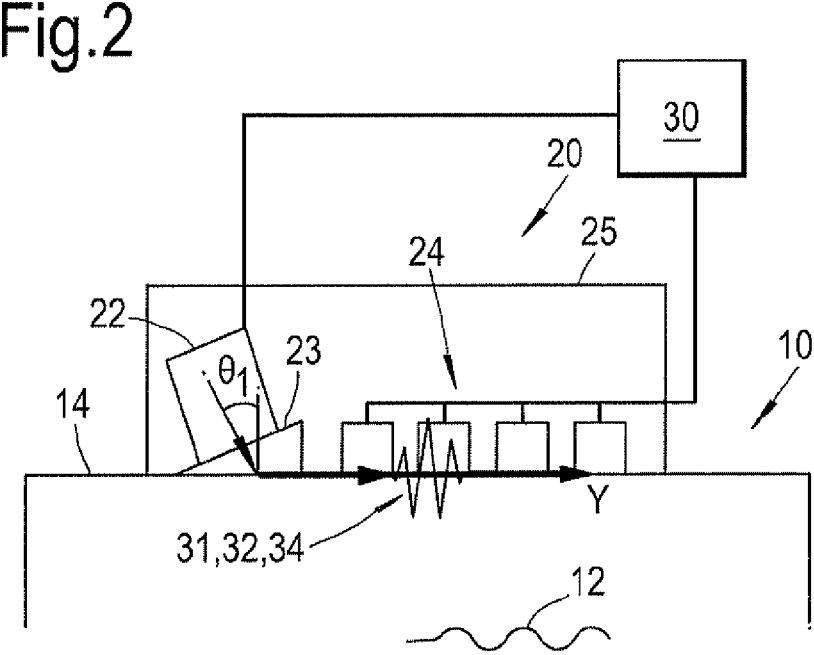
FIG. 2 shows a cross sectional view of a part of the turbine blade of FIG. 1 and a crystallographic orientation measurement assembly.

FIG. 2 shows a radial cross sectional view of part of the turbine blade 10 of FIG. 1. The blade includes a crack 12 located underneath a surface 14 of the blade 10.

In FIG. 2, a crystallographic orientation measurement assembly 20 is in contact with the surface 14 of the blade 10. The crystallographic orientation measurement assembly 20 comprises an ultrasonic transducer 22 and a detector array 24, each being in contact with the surface of the blade 10. In this embodiment, the transducer 22 and the detector array 24 are housed within a casing 25, though in some cases the casing may not be provided.

The transducer 22 is configured to generate surface ultrasonic waves in the surface 14 of the blade 10 and is mounted to the surface 14 at an angle θ to the surface 14 by a wedge 23 made of an ultrasonic transmissive material such as Perspex. The ultrasonic waves produced by the transducer 22 are transmitted through the wedge 23 to the surface 14 of the component at an incident angle $\theta_1$. This ensures that a required surface wave is generated with maximum efficiency. For example, where the required surface wave is a Rayleigh wave, the incident angle $\theta_1$ for producing Rayleigh waves at maximum efficiency is given by the formula:

$$\sin(\theta_I) = \frac{V_I}{V_R}$$

Where $V_R$ represents the Rayleigh wave velocity in the material of the object to be measure (i.e. the blade 10 in this example) and $V_I$ represents the incident wave velocity in the material of the wedge, which in this example comprises Perspex™. The generation of the surface wave may not be 100% efficient however, such that some bulk waves are produced by the transducer 22. The wedge may be shaped such that the transducer is mounted to the blade 10 at a preset angle $\theta_1$ which corresponds to the above formula for a particular known material. Alternatively, the wedge 23 may be adjustable such that the assembly 20 can be used for objects comprising different materials.

The ultrasonic transducer 22 is generally configured to produce surface waves having a frequency of between 1 MHz and 15 MHz, and preferably a frequency of approximately 5 MHz, though different frequencies may be used depending on various conditions, and the properties of the material under investigation. For example, firstly the ring down frequency of single crystal Nickel super alloys (i.e. the material that turbine blades are normally formed of) has been found to be 10 MHz. By choosing a frequency that is substantially higher or lower than this frequency, the noise can be reduced. Secondly, as shown below, the minimum separation between the transducer 22 and the detector array 24 that provides high accuracy is dependent on the frequency used. A higher frequency will generally result in a smaller minimum separation. Thirdly, the frequency generated by the transducer 22 should be matched to the receiving frequency response of the detecting array 24. Most commercially available ultrasonic detectors have a frequency response in the range 5 to 15 MHz, with a peak detection efficiency of around 10 MHz. A frequency of 5 MHZ is therefore chosen in order to obtain a good compromise between each of these requirements.

Figure 3:
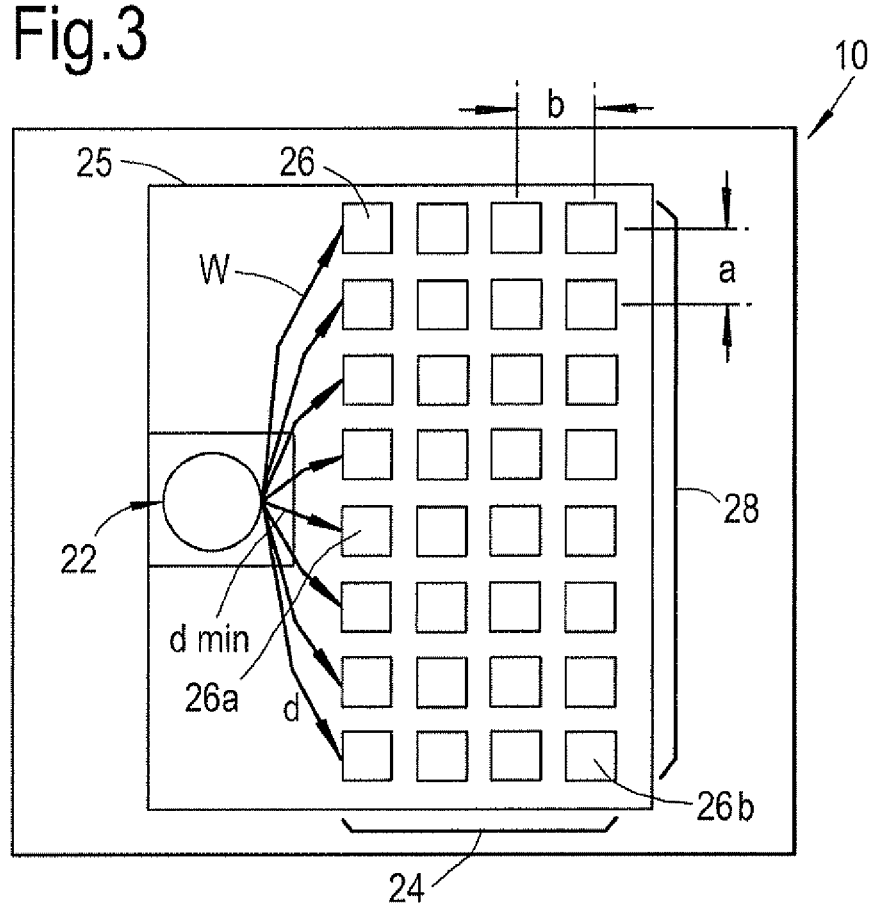
FIG. 3 shows a plan view of the assembly of FIG. 2.
Figure 4:
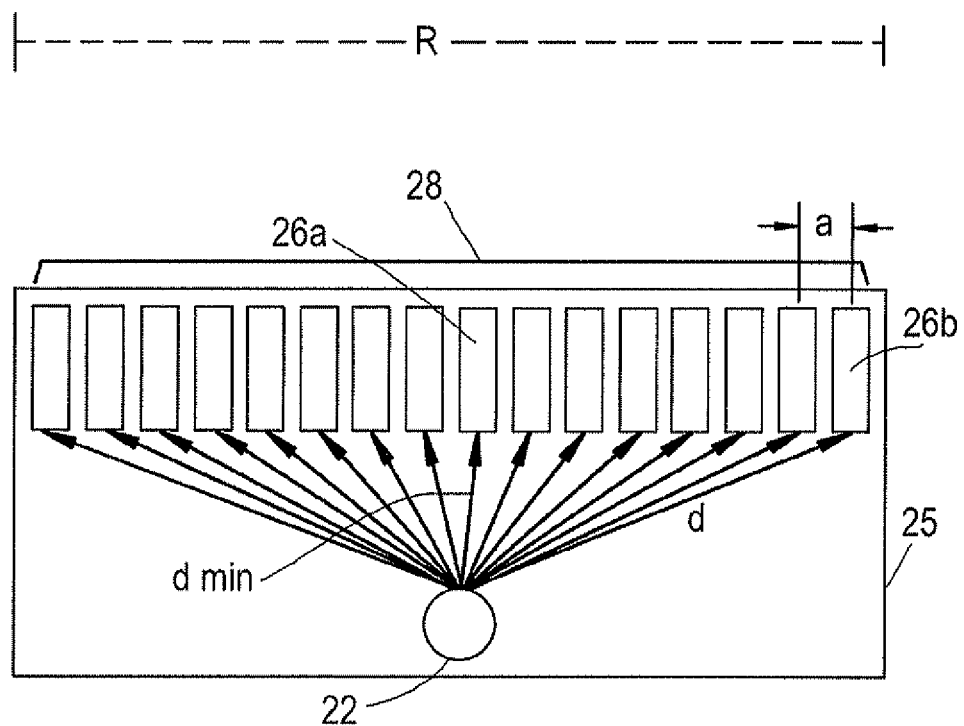
FIG. 4 shows a plan view of an alternative crystallographic orientation measurement assembly.

As shown in detail in FIG. 3, the detector array 24 comprises a plurality of ultrasonic detectors 26 arranged in a plurality of rows 28. Such an arrangement is known as a "2-d" array. One example of a suitable 2-d detector array is provided by Imasonic™ of Besancon, France. An example of a "1-d" array is shown in FIG. 4, and comprises a single row 28 of ultrasonic detectors 26. Each of the detectors 26 is configured to detect the surface waves generated by the transducer 22. The detectors 26 are configured to send a signal representative of the amplitude of the wave to a controller 30 (described in greater detail below).

The centre of each of the detectors 26 in the array 24 is separated from the adjacent detectors 26 in each row 28 by a known distance a, and each row 28 is separated by a known distance b. The physical size of the array 24 is therefore related to the distances a and b, and the number of detectors 26 in the array 24. Generally, the resolution and focusing ability of the array is proportional to the total aperture, i.e. size of the array. In other words, the resolution of the detector array 24 is proportional to the number of detectors 26 in the array 24, and the distance between the detectors 26, known as "pitch". The resolution can therefore be increased by either increasing the number of detectors 26 in the array 24, or by increasing the pitch. However, the number of detectors 26 in the array 24 is limited by the number of channels in the controller 30. On the other hand, beyond a certain value, an increase in pitch will lead to "side lobes", also known as "grating lobes" being generated in addition to the main lobe as a result of the detector array 24 acting as a diffraction grating. Such grating lobes may result in image artefacts and consequently a reduction in resolution. Grating lobes can be avoided or minimized by limiting the pitch to half a wavelength of the surface waves generated by the transducer 22. The wavelength is given by the wave velocity in the material under investigation divided by the frequency of the surface waves. In this example therefore, where the frequency generated by the transducer 22 is approximately 5 MHz and the wave velocity is approximately 6000 meters per second, the pitch, i.e. distances a and b are both approximately 0.6 mm. Where the frequency generated by the transducer 22 is approximately 10 MHz, the pitch is approximately 0.3 mm.

Each detector 26 in the detector array 24 is separated from the transducer 22 by a distance d. The distance d varies for each detector 26, from a minimum value $d_{min}$ for the detector 26a in the array 24 which is closest to the transducer 22, to a maximum value $d_{max}$ for the detector 26b in the array 24 which is furthest from the transducer 22.

The transducer 22 and detector array 24 are each connected to the controller 30, as shown diagrammatically in FIG. 2. The controller 30 is electrically connected to the transducer 22 and each detector 26 of the array 24. The controller 30 provides a single voltage spike or a half-cycle square wave to the transducer. This causes the transducer element to vibrate at its resonant frequency. The pulse length is controlled by a damping material provided on the back of the transducer 22, i.e. on the side of the transducer that does not come into contact with the wedge 23. The controller 30 also receives signals representing the amplitude of the surface and bulk waves detected by the detectors 26. An example of a suitable controller 30 is the Micropulse™ MP5PA array controller manufactured by Peak NDT Ltd of Derby, UK. This controller is has been chosen, as is provides fully parallel channels, rather than using multiplexing to aggregate the signals from each of the detectors 26 in the array 24 into a single signal. This allows signals from individual detectors 26 to be recorded, which allows a crystallographic orientation to be determined.

The crystallographic orientation of an object such as the blade 10 can be determined using the crystallographic orientation measurement assembly 20 using the following method.

First, the distance $d_{min}$ between the transducer 22 and the detector 26a in the array 24 which is closest to the transducer 22 must be determined using the following method.

Figure 5:
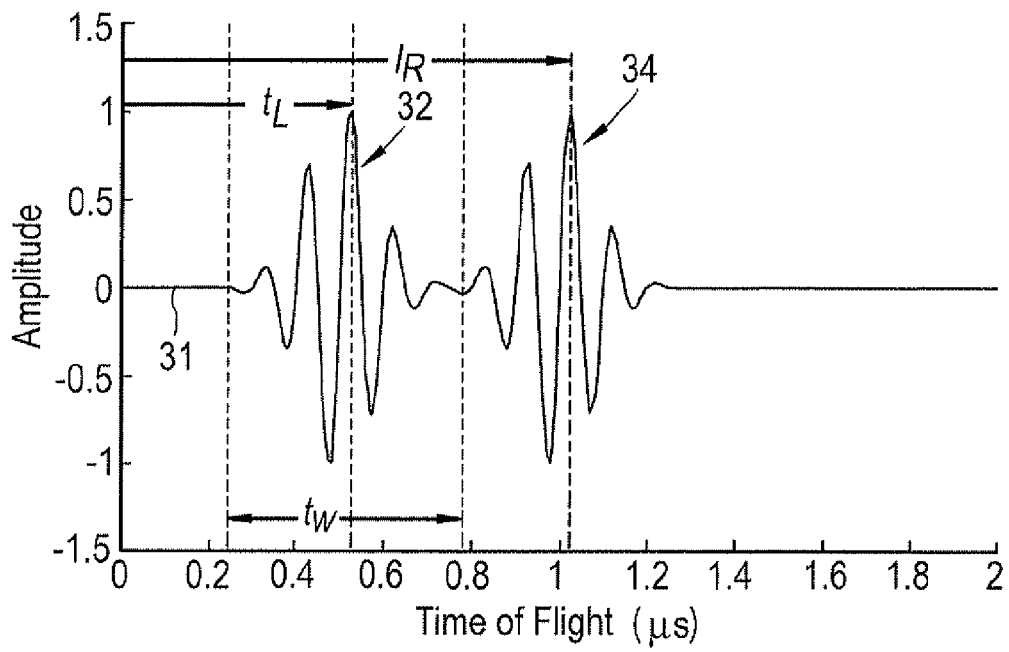
FIG. 5 shows a graph of surface wave amplitudes plotted against time at a point on an object for an ideal mechanically and electrically shielded crystallographic orientation measurement assembly.

FIG. 5 shows simulated data comprising surface wave amplitudes transmitted through an anisotropic object plotted against time at a distance d from a transducer which produces an ultrasonic wave 31 having a pulse length/duration $t_w$. It has been found that surface waves generated by a surface mounted transducer comprise a number of different wave types, in particular, longitudinal surface waves 32 and Rayleigh waves 34. These different wave types initially overlap, and then spread out as the wave travels from the transducer 22 across the surface of the object 10. This is because the different wave types travel at different speeds. The longitudinal surface wave 32 has been found to have a higher velocity $c_L$ in a given material compared to the velocity $c_R$ of the Rayleigh waves, and so the longitudinal surface wave 32 arrives at the distance d earliest in the time-trace, while the lower velocity Rayleigh wave 34 arrives later, as shown in FIG. 5.

For accurate velocity measurement at a distance d of either the longitudinal 32 or Rayleigh 34 waves, the waves 32, 34 need to be separated from one another at the distance d. For this to occur, the time-of-flight of the Rayleigh wave, $t_R$, needs to be at least the time-of-flight of the longitudinal wave, $t_L$, plus the pulse-length of the signals, $t_w$. This is given mathematically as:

$$t_R = t_L + t_w \tag{1}$$

The times-of-flight of the transmitted waves 32, 34 are given by the distance d between the transducer 22 and the respective detectors 26, and the velocity c of the waves 32, 34, thus:

$$t_L = \frac{d}{c_L} \tag{2}$$

$$t_R = \frac{d}{c_R} \tag{3}$$

where the subscripts L and R refer to the longitudinal and Rayleigh waves respectively.

The pulse-length $t_w$ is approximately the number of cycles n in the ultrasonic wave 31 divided by the centre frequency $f_c$ of the wave 31:

$$t_w \approx \frac{n}{f_c} \tag{4}$$

Therefore, substituting Equations 2-4 into Equation 1 yields:

$$\frac{d}{c_R} = \frac{d}{c_L} + \frac{n}{f_c} \tag{5}$$

Arranging the above equation to make the distance the subject yields:

$$d = \frac{n}{f_c} \left( \frac{c_L c_R}{c_L - c_R} \right) \tag{6}$$

Therefore, the above equation gives the minimum distance $d_{min}$ that the transducer 22 and the detector 26a in the array 24 which is closest to the transducer 22 have to be separated to ensure the signals are time resolvable and hence an accurate velocity measurement, and therefore crystallographic orientation measurement, can be made. In contrast, in previous methods, where no minimum distance $d_{min}$ is determined, the distance between the transducer 22 and the detector 26a may be less than the minimum distance, and as such the longitudinal and Rayleigh waves 32, 34 become hard to distinguish from one another, resulting in a high apparent noise to signal ratio.

On the other hand, the maximum distance is limited by the component size. Generally, as will be understood from basic trigonometry, the range of angles Δα over which the velocity profile is measured for an array 24 having a given width r (i.e. the distance a times the number of detectors 26) is related to $d_{min}$:

$$\Delta \alpha = 2\tan^{-1}\left(\frac{0.5r}{d_{min}}\right)$$

As will be understood from the above equation, a larger $d_{min}$ will correspond to a smaller range of angles over which the velocity profile is measured for an array 24 having a given width r. Measuring the angles over a smaller range will reduce the orientation measurement accuracy. As a result, the distance $d_{min}$ should be as small as possible, while being at least the smallest value that allows the signals to be time resolvable.

In anisotropic materials, the times of flight $t_L$, $t_R$ of the surface waves 32, 34 are dependent somewhat on the direction of travel of the waves 32, 34 relative to the crystallographic orientation of the material. Since at this point in the method the crystallographic orientation is unknown, the distance $d_{min}$ is determined on the basis of the minimum time of flight $t_R$ of the Rayleigh waves 34, and the maximum time of flight $t_L$, of the longitudinal waves 32, i.e. the time of flight where the direction of travel of the respective wave 32, 34 relative to the crystallographic orientation results in the highest Rayleigh wave velocity $c_R$, and the lowest longitudinal wave velocity $c_L$. In this way, when the assembly 20 is used to measure the crystallographic orientation of an object, the Rayleigh and longitudinal waves 32, 34 are separated in the time trace where the detector 26a and the transducer 22 are separation by $d_{min}$.

The above example assumes that there is no "ringing" due to electrical and mechanical coupling or "cross-talk" between the transducer 22 and detectors 26. The assembly is configured such that they are electrically and/or mechanically isolated from each other as far as possible in order to minimize the cross-talk. For example, a barrier (not shown) made of highly attenuating material is placed between the transducer 22 and the detector array 24. The transducer 22 and the detector array 24 are electrically shielded by covering their two housings in an electrically conductive paint. However, in any practical crystallographic orientation measurement assembly 20 there will always be a finite amount of ring-down (as represented by wave 33 in FIG. 6), as the transducer 22 and detectors 26 can never be completely mechanically and electrically decoupled.

Figure 6:
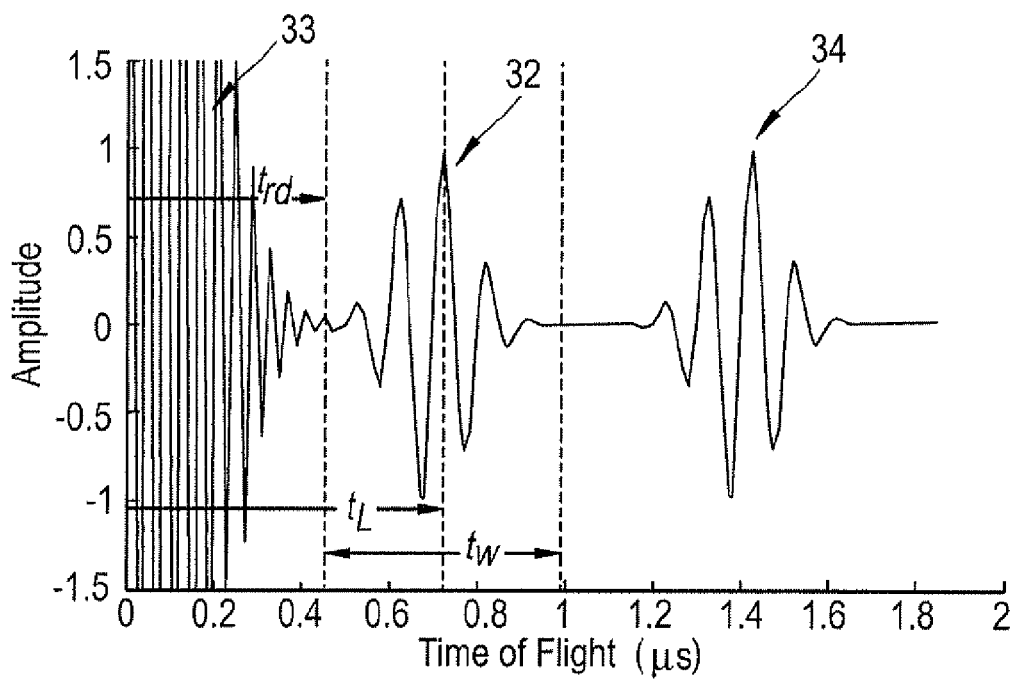
FIG. 6 shows a graph of surface wave amplitudes plotted against time at a point on an object for a crystallographic orientation measurement assembly having mechanical and/or electrical cross talk between components of the assembly.

FIG. 6 shows simulated data comprising surface wave amplitudes transmitted through an anisotropic object plotted against time at a distance d from a transducer which produces an ultrasonic wave, where the transducer 22 and detectors 26 are not wholly mechanically and electrically decoupled.

To ensure sufficient separation of the longitudinal 32 and Rayleigh 34 waves in this case, the time-of-flight of the longitudinal wave 32 has to be at least the ring-down time, $t_{rd}$, plus half the pulse-length $t_w$, thus:

$$t_L = t_{rd} + \frac{t_w}{2} \quad (7)$$

Substituting Equation 2 and 4 into Equation 7 and rearranging for distance yields:

$$d = c_L\left(t_{rd} + \frac{n}{2f_c}\right) \quad (8)$$

Thus, the minimum distance $d_{min}$ between the transducer 20 and the detector 26a in the array 24 which is closest to the transducer 22 is given by the greater value of Equations 6 and 8 and is thus dependent on the velocity of the ultrasonic waves 32, 34 and the duration of the ring-down $t_{rd}$.

In practical terms, $d_{min}$ may be found experimentally for a given material or batch of components. In one example, where the object to be measured is a single crystal turbine blade 10 comprising a nickel based superalloy such as CMSX-4, $d_{min}$ has been found to be approximately 3 mm where the surface wave generated by the transducer 22 has a frequency of 5 MHz. CMSX-4 is a high Nickel content alloy having the following composition by weight: Nickel: 61.7%, Cobalt: 9%, Chromium: 6.5%, Tantalum: 6.5%, Tungsten: 6%, Aluminium: 5.6, Rhenium: 3%, Titanium: 1%, Molybdenum: 0.6%, Hafnium: 0.1%.

The assembly 20 can be used to determine the crystallographic orientation of an object such as a turbine blade 10 as follows.

The minimum separation distance $d_{min}$ is first determined. $d_{min}$ may be determined experimentally, by measuring the longitudinal and Rayleigh wave velocities $c_L$, $c_R$ and ring down time $t_{rd}$, and using equations 6 and 8 to determine $d_{min}$ for the object to be measured, or for a batch of object. Alternatively, $d_{min}$ may be determined separately for a particular material and provided to the user in a look up table. The user can then use the appropriate minimum separation on the basis of the look up table.

Once $d_{min}$ has been determined, the user then places the transducer 22 and the detector array 24 on the surface 14 of the blade 10 such that the distance between the detector 26a of the detector array 24 closest to the transducer 22 is at least $d_{min}$. In some cases, the detector array 24 may be placed a greater distance from the transducer 22 than $d_{min}$. $d_{min}$ therefore represents the closest distance that the transducer 22 and the detector 26a can be placed while providing a reliable indication of wave velocities and therefore crystallographic orientation. In some cases, the casing 25 may be configured such that the transducer 22 and the detector array 24 are separated by at least the required distance $d_{min}$ for a predetermined experimental set up for a particular material to be measured. The casing 25 may also be adjustable such that an appropriate separation can be selected for a particular material on the basis of the lookup table or experimentation using a calibration procedure. The calibration procedure could be used in addition to the lookup table to account for manufacturing variations.

Once the assembly 20 is placed in contact with the surface 14, the controller 30 is then actuated to generate a voltage spike (as described above) to the transducer 22 such that the transducer 22 produces an ultrasonic signal having a required centre frequency $f_c$. The controller 30 records the time at which the signal is sent, which can be represented at t=0.

The surface waves 32, 34 then travel across the surface 14 of the blade 10, as shown by the arrows W in FIG. 3. When the waves 32, 34 reach the respective detectors 26 in the array 24, the detectors are caused to generate a signal which is transmitted to the controller 30. The controller 30 records the times at which the surface waves 32, 34 are received at each detector 26 to produce time of flight data. The time of flight data could comprise both the longitudinal and Rayleigh waves 32, 34. It has been found that more accurate results can be determined using only the longitudinal surface waves 32.

The crystallographic orientation of the blade 10 can then be determined using this data as follows. An initial estimate of the crystallographic orientation of the blade 10 is made to compute the velocity profile relative to the array 24. A propagation model uses this velocity profile to compute the time of flight data. The measured and computed time of flight data are then compared to find the global error for the estimated orientation. The process is then repeated with different orientations until the global error is minimized. The orientation at which the global error is minimized therefore corresponds to the crystallographic orientation of the material.

The same assembly 20 can then be used to detect defects such as cracks 12. The array 24 is used to generate bulk waves in the blade 10 (since the transducer 22 is configured to only produce surface waves). The reflected bulk waves can be detected by the detector array 24 to detect defects using conventional ultrasonic techniques.

The invention therefore provides an assembly and a method of measuring a crystallographic orientation in an anisotropic material such as a directionally solidified or single crystal alloy turbine blade. The same assembly can also be used to detect sub-surface defects in the object, thereby reducing time and costs. Furthermore, the assembly and method can be used to determine the location of defects to a relatively high degree of precision due to the high resolution of the detector array.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

The invention claimed is:

1. A method of measuring a crystallographic orientation of an object using an ultrasonic transducer and a detector array comprising a plurality of ultrasonic detectors, the method comprising:
   determining a minimum distance ($d_{min}$) between the transducer and a detector of the detector array closest to the transducer;
   placing the transducer and the detector array in contact with a surface of the object such that the transducer and the detector of the detector array closest to the transducer are separated by at least the minimum distance ($d_{min}$);
   using the transducer to generate an ultrasonic surface wave pulse in the surface of the object, the ultrasonic surface wave pulse having a pulse duration ($t_w$) and comprising a longitudinal surface wave and a Rayleigh wave; and
   measuring a time of flight of a surface wave generated by the transducer between the transducer and each detector of the array to determine the crystallographic orientation of the object;
   wherein the minimum distance ($d_{min}$) is the distance at which the minimum time of flight of the Rayleigh wave ($t_R$) is at least the sum of the maximum time of flight of the longitudinal surface wave ($t_L$) and the maximum pulse duration ($t_w$).

2. A method according to claim 1, where the ultrasonic surface wave pulse has a centre frequency ($f_c$) and a pulse length (n) cycles, the longitudinal surface wave has a minimum velocity in the object ($c_L$), and the Rayleigh wave has a maximum velocity in the object ($c_R$), wherein the minimum distance ($d_{min}$) is determined by the formula:

$$d_{(min)} = \frac{n}{f_c}\left(\frac{c_L c_R}{c_L - c_R}\right).$$

3. A method according to claim 2, wherein the detector array has a ring down time ($t_{rd}$), and the distance ($d_{min}$) is determined by the greater value of $d_{min}$ determined by the formulas:

$$d_{(min)} = \frac{n}{f_c}\left(\frac{c_L c_R}{c_L - c_R}\right)$$

and;

$$d_{(min)} = c_L\left(t_{rd} + \frac{n}{2f_c}\right).$$

4. A method according to claim 1, wherein the ultrasonic surface wave pulse has a frequency in range 1 MHz to 15 MHz.

5. A method according to claim 4, wherein the ultrasonic surface wave pulse has a frequency of approximately 5 MHz.

6. A method according to claim 1, wherein the object comprises a nickel based alloy.

7. A method according to claim 1, wherein the object is a component of a gas turbine engine.

8. A method according to claim 7, wherein the component is a turbine blade.

9. A method according to claim 1, wherein the detector array comprises a 1-d array in which the detectors are arrayed in a row.

10. A method according to claim 1, wherein the detector array comprises a 2-d array in which the detectors are arrayed in at least two rows.

11. A crystallographic orientation measurement assembly, the assembly comprising:
   an object having a crystallographic orientation;
   an ultrasonic transducer configured to generate an ultrasonic surface wave pulse having a pulse duration ($t_w$), the ultrasonic surface wave pulse comprising a longitudinal surface wave and a Rayleigh wave; and
   a detector array comprising a plurality of ultrasonic detectors; wherein
   the transducer and the detector of the detector array closest to the transducer are separated by at least a minimum distance ($d_{min}$), wherein the minimum distance ($d_{min}$) is the distance at which the minimum time of flight of the Rayleigh wave ($t_R$) is at least the sum of the maximum time of flight of the longitudinal surface wave ($t_L$) and the maximum pulse duration ($t_w$).

* * * * *